United States Patent
Fetzner et al.

(10) Patent No.: US 9,995,675 B2
(45) Date of Patent: Jun. 12, 2018

(54) DEVICE FOR DETERMINING THE CONCENTRATION OF AT LEAST ONE GAS IN A SAMPLE GAS FLOW BY MEANS OF INFRARED ABSORPTION SPECTROSCOPY

(71) Applicant: AVL EMISSION TEST SYSTEMS GMBH, Neuss (DE)

(72) Inventors: Stephan Fetzner, Forst (DE);
Raimund Brunner, Breisach (DE);
Ulrich Ulmer, Freiburg (DE)

(73) Assignee: AVL EMISSION TEST SYSTEMS GMBH, Neuss (DE)

( * ) Notice: Subject to any disclaimer, the term of this patent is extended or adjusted under 35 U.S.C. 154(b) by 55 days.

(21) Appl. No.: 15/112,690

(22) PCT Filed: Jan. 22, 2015

(86) PCT No.: PCT/EP2015/051205
§ 371 (c)(1),
(2) Date: Jul. 20, 2016

(87) PCT Pub. No.: WO2015/110503
PCT Pub. Date: Jul. 30, 2015

(65) Prior Publication Data
US 2017/0010207 A1 Jan. 12, 2017

(30) Foreign Application Priority Data
Jan. 22, 2014 (DE) .......................... 10 2014 100 691

(51) Int. Cl.
*G01N 21/03* (2006.01)
*G01N 21/3504* (2014.01)
(Continued)

(52) U.S. Cl.
CPC ...... *G01N 21/3504* (2013.01); *G01N 21/0332* (2013.01); *G01N 33/0016* (2013.01); *G01N 21/031* (2013.01); *G01N 21/05* (2013.01)

(58) Field of Classification Search
CPC ............... G01N 21/35; G01N 21/3504; G01N 21/0332; G01N 21/031
See application file for complete search history.

(56) References Cited

U.S. PATENT DOCUMENTS 4,914,297 A * 4/1990 Wieboldt ................. G01N 5/04
250/343
5,223,716 A  6/1993 Rossiter
(Continued)

FOREIGN PATENT DOCUMENTS

DE         100 01 382 A1   9/2000
DE   10 2005 033 267 A1   2/2006
(Continued)

*Primary Examiner* — Casey Bryant
(74) *Attorney, Agent, or Firm* — Norman B. Thot

(57) ABSTRACT

A device for determining a concentration of at least one gas in a sample gas flow by infrared absorption spectroscopy. The device includes a gas cell which includes a thermal insulation, a chamber, a heating source arranged within the thermal insulation which heats the sample gas flow to a desired temperature, and a sample gas duct having an outlet. The sample gas duct is heated by the heating source upstream of the outlet. An infrared radiation source emits a radiation which is conducted through the chamber of the gas cell. The sample gas flow is conducted into the chamber and into the radiation. A detector has the radiation exiting the chamber conducted thereto to determine an absorption spectrum.

13 Claims, 3 Drawing Sheets

(51) Int. Cl.
*G01N 33/00* (2006.01)
*G01N 21/05* (2006.01)

(56) References Cited

U.S. PATENT DOCUMENTS

| | | | |
|---|---|---|---|
| 5,500,768 A * | 3/1996 | Doggett | G01N 21/274 359/652 |
| 5,964,712 A | 10/1999 | Kubo et al. | |
| 6,250,799 B1 | 6/2001 | Kinoshita et al. | |
| 2005/0092067 A1* | 5/2005 | Petrovic | G01N 21/0303 73/31.05 |
| 2006/0011844 A1 | 1/2006 | Oka et al. | |
| 2006/0263256 A1 | 11/2006 | Koshel et al. | |
| 2009/0153854 A1 | 6/2009 | Taylor-Hayward et al. | |
| 2011/0285998 A1 | 11/2011 | Hara et al. | |
| 2012/0192621 A1 | 8/2012 | Ludwig | |

FOREIGN PATENT DOCUMENTS

| | | |
|---|---|---|
| EP | 1 596 184 A2 | 11/2005 |
| EP | 1 724 567 A1 | 11/2006 |
| EP | 1 788 378 A1 | 5/2007 |
| EP | 2 388 570 A1 | 11/2011 |
| GB | 2 255 194 A | 10/1992 |
| JP | 2000-2656 A | 1/2000 |
| JP | 2000-180356 A | 6/2000 |
| WO | WO 2010/146079 A1 | 12/2010 |

* cited by examiner

DEVICE FOR DETERMINING THE CONCENTRATION OF AT LEAST ONE GAS IN A SAMPLE GAS FLOW BY MEANS OF INFRARED ABSORPTION SPECTROSCOPY

CROSS REFERENCE TO PRIOR APPLICATIONS

This application is a U.S. National Phase application under 35 U.S.C. § 371 of International Application No. PCT/EP2015/051205, filed on Jan. 22, 2015 and which claims benefit to German Patent Application No. 10 2014 100 691.7, filed on Jan. 22, 2014. The International Application was published in German on Jul. 30, 2015 as WO 2015/110503 A1 under PCT Article 21(2).

FIELD

The present invention relates to a device for determining the concentration of at least one gas in a sample gas flow by infrared absorption spectroscopy, the device comprising an infrared radiation source, the radiation of which is adapted to be conducted through a chamber of a gas cell, a sample gas flow which is adapted to be conducted into the chamber and through the radiation, a detector onto which the radiation exiting the chamber is adapted to be conducted and by which the absorption spectrum of the exiting radiation is adapted to be determined, and a heat source via which the sample gas flow is heated to a desired temperature.

BACKGROUND

Infrared spectroscopy for determining a concentration of individual gas components has previously been described. The most common methods relate to the Fourier transform infrared spectrometer or the non-dispersive infrared spectrometer. With the development of compact high-power semiconductor lasers, gas analyzers based on the laser spectroscopy have been established to an increasing extent. New laser types, such as quantum cascade lasers, revolutionize laser spectroscopy in the medium infrared range.

All these analyzing methods rely on specific frequency ranges being absorbed during the irradiation of a sample gas with infrared beams. The infrared radiation lies in the range of the oscillation level of the molecular bonds which are induced to oscillate by the absorption. A prerequisite therefor is a dipole moment which is either already present or which is generated in the molecule. The different oscillation states cause absorption losses of the infrared radiation of different optical frequencies. The spectrum in the transmission thus contains individual absorption lines characteristic of the gas so that the sample gas can be examined for the presence of concrete molecules, and their concentration in the sample gas can be determined.

A quantum cascade laser can in particular determine the presence and concentration of pollutant molecules in the exhaust gas of internal combustion engines, such as dinitrogen monoxide, nitrogen monoxide, nitrogen dioxide, carbon dioxide, carbon monoxide and ammonia.

Common laser-spectroscopic systems comprise a laser as a radiation source, the radiation of which is conducted into a gas cell via an optical path. The beam is repeatedly reflected in the gas cell via a suitable mirror configuration. A sample gas flow is introduced at the same time into the gas cell, wherein the radiation of the laser penetrates the sample gas flow and excites the molecules corresponding to the optical frequency. The respective frequency is absorbed due to this excitation energy. The intensity of the transmitted beam decreases at this point in the spectrum. The absorption itself is not defined exactly, but is subject to a broadening due to temperature and pressure changes. The beam having its spectrum changed in this manner exits the measuring cell and impinges upon a detector via which the changed frequency band is evaluated, thus allowing the presence of specific substances and their concentration to be determined. The sample gas flow is usually delivered via a downstream vacuum pump.

The absorption characteristic in the spectrum is evaluated and/or analyzed when determining concentration. This characteristic is generally referred to as the line spectrum of the absorbing gases. It has turned out, however, that the line shape in this spectrum depends on pressure and temperature. For the purpose of evaluation, these parameters must therefore either be kept constant or must be continuously metrologically detected and offset. The gas is therefore conditioned and the pressure and temperature are kept constant in order to increase measuring accuracy. Both the measuring cell and the supply line of the measuring gas must be heated for tempering purposes. The occurrence of temperature gradients must therefore be prevented during the entire sampling process to avoid gas entrainment effects and thermal turbulences which would affect the absorption behavior of the laser radiation during its passage through the medium.

For carrying out such a conditioning of the sample gas, it is common practice to heat the gas cell and the sample gas in advance to a specific temperature. Heating hoses are, for example, used to preheat the sample gas, as is described in EP 2 388 570 A1. The measuring cell as well as the sample gas in the supply hose are heated, for example, to 191° C. While this design helps to improve measuring results, a problem associated with using two different temperature probes and temperature controllers arises so that measuring errors due to temperature gradients occurring between the gas cell and the sample gas flow cannot be completely precluded.

SUMMARY

An aspect of the present invention is to provide a device for determining the concentration of at least one gas in a sample gas flow by infrared absorption via which measuring results can be further improved when compared with known designs by avoiding, as reliably as possible, temperature gradients between the sample gas and the gas cell.

In an embodiment, the present invention provides a device for determining a concentration of at least one gas in a sample gas flow by infrared absorption spectroscopy. The device includes a gas cell comprising a thermal insulation, a chamber, a heating source arranged within the thermal insulation which is configured to heat the sample gas flow to a desired temperature, and a sample gas duct comprising an outlet. The sample gas duct is configured to be heated by the heating source upstream of the outlet. An infrared radiation source is configured to emit a radiation which is conducted through the chamber of the gas cell. The sample gas flow is configured to be conducted into the chamber and into the radiation. A detector is configured to have the radiation exiting the chamber be conducted thereto and to determine an absorption spectrum.

BRIEF DESCRIPTION OF THE DRAWINGS

The present invention is described in greater detail below on the basis of embodiments and of the drawings in which.

DETAILED DESCRIPTION

Figure 1:
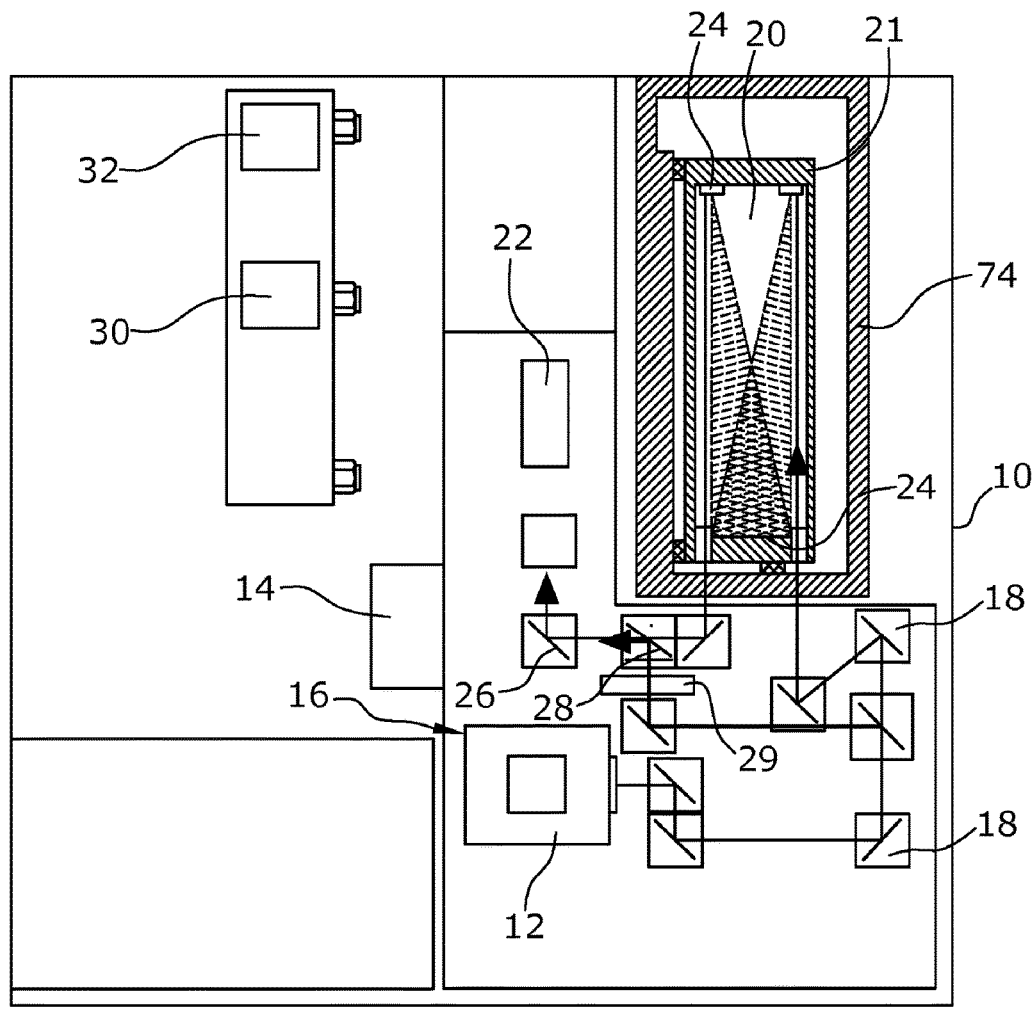
FIG. 1 shows a schematic diagram of a quantum cascade laser.
Figure 2:
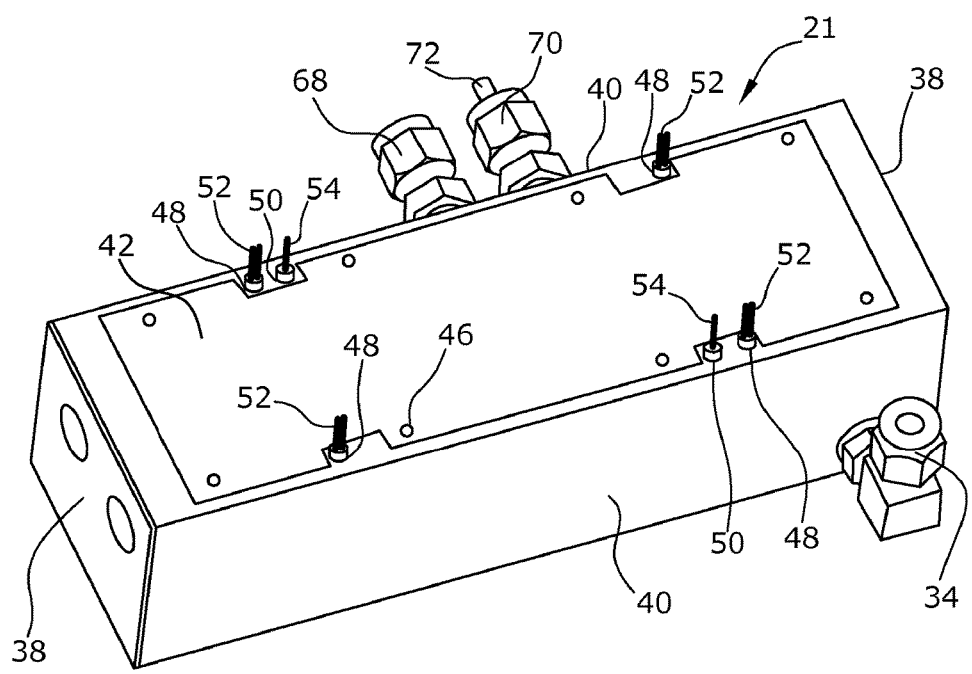
FIG. 2 shows a perspective view of the interior of a gas cell.
Figure 3:
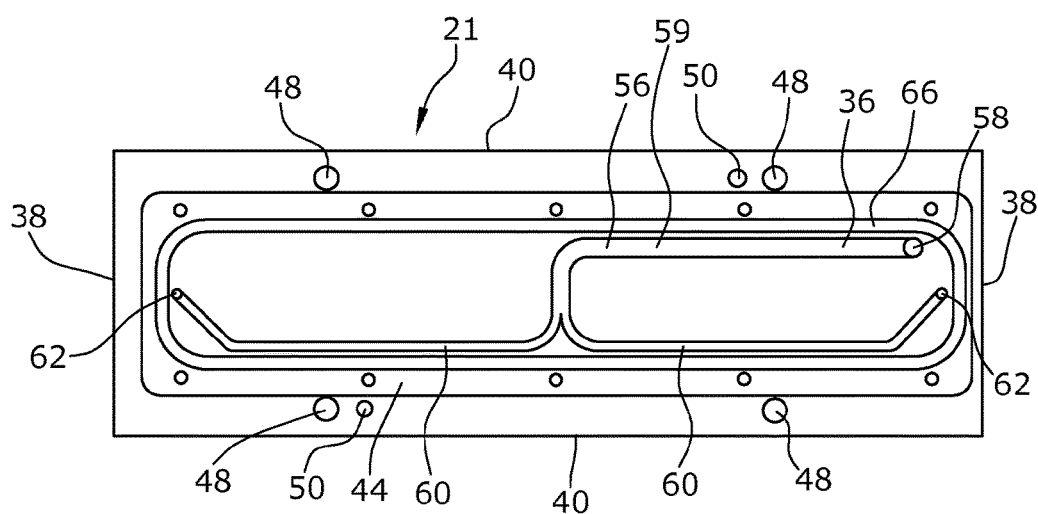
FIG. 3 shows a plan view of the base of the gas cell of FIG. 2.

Since the heating source is arranged within a thermal insulation of the gas cell, wherein, within the thermal insulation, a sample gas duct heated by the heating source is arranged upstream of an outlet into the chamber, it is possible to heat both the sample gas flow and the gas cell by only one heating source. It can thus be provided that no temperature gradient occurs between the sample gas flow flowing into the gas cell and the gas cell. The measuring results are thus improved and the expense for providing for the heating and temperature monitoring is reduced.

In an embodiment of the present invention, the sample gas duct can, for example, be defined at a side of a boundary wall facing away from the chamber. The walls of the gas cell thus act as a heat conductor to heat the sample gas flow and the interior of the gas cell. Temperature differences are thereby avoided in a simple manner.

In an embodiment of the present invention, at least sections of the sample gas duct can, for example, be defined by a recess in the boundary wall of the gas cell. Such a recess can be produced in the boundary wall, for example, by milling. A direct heat contact without transition losses between the sample gas flow and the gas cell is thus established.

In an embodiment of the present invention, the sample gas duct can, for example, extend to both axial ends of the gas cell and can, for example, comprise two outlets each entering the chamber. This introduction of the gas from two sides provides a uniform distribution in the gas cell. Exact results can thereby be quickly obtained.

In an embodiment of the present invention, the run lengths of the sub-ducts extending to the outlets can, for example, be the same. During heating of the sample gas flow in the sub-ducts, it is thus provided that the sample gas flows enter the gas cell at the same end temperature since both comprise the same heat transition surface.

Such same run lengths can, for example, be provided by defining a first sample gas duct section at the boundary wall, which duct section extends to a central axis between the two axial ends of the gas cell, and the first sample gas duct section being divided into the two sub-ducts at the level of the middle between the axial ends, the sub-ducts extending to the axial ends. A duct of a simple configuration thus provides the same maximum run lengths of the two sub-ducts. This run length provides a temperature of the sample gas flowing into the gas cell which corresponds to the temperature within the gas cell.

In an embodiment of the present invention, the sample gas duct can, for example, have a meander-shaped configuration so that a maximum surface of the boundary wall can be utilized to heat the sample gas.

In an embodiment of the present invention, the sample gas duct can, for example, be defined at the base of the gas cell and closed by a base plate. The duct can accordingly be produced by milling and can simply be closed by the lid. An inexpensive manufacture is thus provided as is a very good heat transfer to the sample gas flow.

The sample gas duct also advantageously extends up to a place immediately in front of the axial boundary walls of the gas cell, and the outlets each enter the chamber on the axial central axis of the gas cell. A uniform distribution of the sample gas flow in the gas cell from opposite sides is thereby provided, whereby the exactness of the measuring results is increased.

In an embodiment of the present invention, the outlets of the sample gas duct can, for example, enter the chamber axially between the object or field mirrors and the axial boundary walls so that the sample gas flow is first distributed behind the mirrors before entering the actual measuring zone between the object or field mirrors. This also produces very good measuring results.

In an embodiment of the present invention, the heating source can, for example, be defined by a plurality of electric heating rods or heating mats arranged in the side walls of the gas cell. This leads to a very uniform heat distribution in the walls of the gas cell so that temperature gradients are precluded.

In an embodiment of the present invention, the heating rods can, for example, be arranged in vertical bores in the heating walls. The heating rods, when installed, are easily accessible so that the heating rods can both be connected and exchanged, if necessary, in a simple manner.

A temperature sensor can advantageously be arranged in at least one of the boundary walls, via which temperature sensor the temperature of the gas cell is measured. The heat to be supplied can be controlled depending on the measuring values of this sensor. In this configuration, the sensor serves to both monitor the sample gas temperature and the gas cell temperature so that one sensor is omitted compared with known designs.

The boundary walls are also made of a material with a heat conductivity of more than 12 W/mK. This provides an adequate heat transfer to the sample gas flow so that temperature differences between the gas cell and the sample gas flow are precluded.

A device for determining the concentration of a gas in a sample gas flow by infrared spectroscopy is thus provided, with the aid of which the concentration and the presence of a gas can be detected with a high accuracy and reproducibility since temperature gradients are avoided. A common control of the gas cell temperature and the sample gas temperature further simplifies the design due to omission of an additional sensor, additional heaters, and their controls, so that the device is inexpensive to manufacture.

An exemplary embodiment of the device for determining the concentration of at least one gas in a sample gas flow by infrared absorption spectroscopy according to the present invention is illustrated in the drawings on the basis of an analyzer having a quantum cascade laser, and will be described below.

The device for determining the concentration of at least one gas in a sample gas flow by infrared absorption spectroscopy according to the present invention is designed as a quantum cascade laser absorption spectrometer in the present exemplary embodiment. The latter is constituted of a housing 10 in which a quantum cascade laser 12 made up of semiconductor layers is arranged as an infrared radiation source, which can be operated either continuously or in a pulsed manner, and which in particular emits radiation in the medium infrared range. It is controlled via a current driver 14 and cooled via a Peltier element 16.

The beam of the laser 12 is conducted into a measuring chamber 20 of a gas cell 21 via a plurality of mirrors 18 or is alternatively directly conducted to the detector 22 via the mirrors 18, which detector can, for example, be an MCT (mercury cadmium telluride) detector that is in particular suitable for the photovoltaic detection in the medium infrared range, and where an incident light quantum is directly converted into a measurable photocurrent. In the measuring chamber 20, this beam is repeatedly reflected at object or field mirrors 24, thus penetrating a sample gas delivered into the measuring chamber 20. This leads to an absorption of the beam in specific frequency ranges of the emitted light band, which is characteristic of the presence and concentration of specific molecules. After the beam has been repeatedly reflected at the object or field mirrors 24, it exits the gas cell 21 and is again supplied to the detector 22 via subsequent mirrors 26. One of these mirrors is configured as a folding mirror 28 so that, depending on the position thereof, either a reference laser beam travels to the detector 22 via a reference gas source 29, or the beam passes through the gas cell 21.

The optical frequency band measured by the detector 22 comprises gaps produced by the absorbed radiation, the size and the depth of the gaps being a measure of the concentration of the gas absorbing in this frequency range. The corresponding conversion is carried out in a known manner by applying the Lambert-Beer law. The emitted wavelength of the laser 12 can be adjusted so that the absorption range of a specific absorption line of the gas component can be selectively swept, whereby cross sensitivities to other gas components are avoided. Gaps in the wavelength range of approximately 10 µm thus occur, for example, in the presence of ammonia.

It must be taken into account, however, that a reliable measurement is possible only in the case of a proper tuning between the path length of the beam and the expected concentration of the molecule to be measured in the sample gas flow so that either an undiluted or a diluted sample gas flow must be used. The measuring conditions must also be kept constant. It is in particular required that the temperature of the sample gas flow and the measuring chamber 20 and/or the gas cell 21 be kept constant since the absorption of the laser beam is caused by excitation of the molecules, which also changes with changes in the temperature. Exact measuring results can accordingly be attained only at constant temperature conditions. The optimum temperature further depends on the degree of dilution of the gas. It has turned out that measurements at a constant temperature of 191° C. in the case of raw gas and of 60° C. in the case of diluted gas produce very good measuring results.

The sample gas is delivered by a vacuum pump 30 with the aid of which the sample gas flow is sucked into the measuring chamber 20. The entire beam path is purged with a gas which does not contain any molecules of the gas to be measured, normally with nitrogen, to avoid a falsification of the measuring results.

A sample gas inlet branch 34 is defined at the gas cell 21 which is connected with a sample gas source, such as, for example, an exhaust gas duct of an internal combustion engine or which is connected with a source containing an already diluted sample gas via a hose (not shown in the drawings). Using the vacuum pump 32, the sample gas is thus sucked from the inlet branch 34 to the vacuum pump 32 via a sample gas duct 36 and the measuring chamber 20.

The gas cell 21 essentially has a parallelepipedal shape so that the measuring chamber 20 is delimited by six boundary walls 38, 40, 42, 44. Two of the boundary walls serve as axial side walls 38 at the axial ends behind the object or field mirrors 24 and are fastened by screws to the lateral side walls 40 which define the lateral boundary. The laser beam is reflected between these axial side walls 38 at the axial ends. The gas cell 21 is delimited towards the top by a lid 42 which serves as a boundary wall and which is screwed to the side walls 38, 40, towards the bottom by a base 44. Besides the bores 46 in the lateral side walls 40 required to fasten the lid 42, three further bores 48, 50 are each defined in the two side walls, which further bores 48, 50 extend vertically to the base 44 and which are open towards the top. In two of these further bores 48, each of the electric heating rods 52 serving as a heating source are arranged, each being arranged at a distance of approximately a quarter of the overall length of the lateral side walls 40 to the axial side walls 38. In each lateral side wall 40, a further bore 50 for receiving a temperature sensor 54 is additionally defined. The boundary walls 38, 40, 42, 44 are made of metal with a good conductivity of at least 12 W/mK so that a heating of the boundary walls 38, 40, 42, 44 and the measuring chamber 20 which is as rapid as possible can be provided.

At the side of the base 44 facing away from the measuring chamber 20, the sample gas duct 36 is milled in the form of a recess 56 in the wall surface. The sample gas duct 36 extends from the sample gas inlet branch 34 to an inlet opening 58 in the base 44 via a bore in the lateral side wall 40, the inlet opening 58 being located in the area of a first axial end of the gas cell 21. From there a first sample gas duct section 59 of the sample gas duct 36 extends in parallel to the lateral side wall 40, then undertakes a 90° bend approximately in the middle between the two axial side walls 38 so that it then extends in parallel to the axial side walls 38 between the two lateral side walls 40. Before it reaches the opposite lateral side wall 40, the sample gas duct 36 is divided into two sub-ducts 60 which extend in opposite 90° bends as continuing sections of the sub-ducts extending straight and in parallel to the lateral side walls 40 so that each sub-duct extends towards the axially delimiting axial side walls 38. Shortly before reaching these axial side walls 38, each one of the sub-ducts 60 is kinked so that they enter an outlet 62, each approximately on the central axis of the gas cell 21 immediately in front of the axial side walls 38. The width of the sub-ducts 60 approximately correspond to half the upstream sample gas duct 36 so that the same flow resistances caused by the same run lengths and cross-sections produce two approximately identical sub-flows which flow into the measuring chamber 20 via the two outlets 62. The inflow takes place axially between the axially delimiting side wall and the upstream object or field mirrors 24 so that a distribution in the measuring chamber 20 is performed before the sample gas enters the area illuminated by the laser beam. Inaccuracies due to uneven distribution of the sample gas flow or flow velocity differences are thus avoided. The milled sample gas duct 36 is closed by a base plate (not shown in the drawings) which is screwed on, whereby the sample gas duct 36 is delimited on all sides. Circumferential seals 66 are of course arranged around the sample gas duct 36 at the locating surface of the base plate as well as at the locating surface of the lid 42.

An outlet branch 68 is arranged approximately in the middle between the axial side walls 38 at the lateral side wall 40 opposite to the sample gas inlet branch 34 via which outlet branch 68 the sample gas flow is extracted from the measuring chamber 20. A connecting branch 70 is located next to this outlet branch 68 in which a temperature sensor 72 is inserted that projects into the measuring chamber 20 to measure the there prevailing temperature.

The entire gas cell 21 is arranged within a thermal insulation 74 which provides that the same temperature prevails in the measuring chamber 20 as in the boundary walls 38, 40, 42, 44. Heating of the entire gas cell 21 and thus both the sample gas duct 36 and the measuring chamber 20 is carried out by the same heating source so that the sample gas flow and the temperature in the measuring chamber 20 are jointly controlled. Since the sample gas duct in the base is selected to be long enough, it is provided that the sample gas taken in has the same temperature as prevails in the measuring chamber 20 before it enters the measuring chamber 20. By using a single temperature controller, temperature gradients between the introduced gas and the interior of the cell are thus reliably avoided, whereby exact measuring results can be obtained. Energy is additionally saved due to a heating process without subsequent losses via lines.

It should be appreciated that the present invention is not limited to the described exemplary embodiment, but that various modifications are possible which also fall within the scope of protection of the appended claims. The duct may thus be configured in a different manner in the area of the gas cell or have another configuration, such, for example, as a meander-shaped configuration. Design changes of the gas cell are also possible. This type of heating is not limited to the use with a quantum cascade laser, but may also be used for other infrared absorption spectrometers.

What is claimed is:

1. A device for determining a concentration of at least one gas in a sample gas flow by infrared absorption spectroscopy, the device comprising:
   a gas cell comprising,
      a thermal insulation,
      a chamber,
      a boundary wall,
      two axial ends,
      a heating source configured to heat the sample gas flow to a desired temperature, the heating source being arranged within the thermal insulation, and
      a sample gas duct comprising two outlets, the sample gas duct being defined at a side of the boundary wall which faces away from the chamber, the sample gas duct being configured to extend to the two axial ends of the gas cell and to be heated by the heating source upstream of the two outlets;
   an infrared radiation source configured to emit a radiation which is conducted through the chamber of the gas cell; and
   a detector configured to have the radiation exiting the chamber be conducted thereto and to determine an absorption spectrum,
   wherein, the sample gas flow is configured to be conducted through the sample gas duct to the two outlets and through the two outlets into the chamber and into the radiation.

2. The device as recited in claim 1, wherein,
   the boundary wall comprises a recess, and
   at least sections of the sample gas duct are defined by the recess.

3. The device as recited in claim 1, wherein,
   the sample gas duct further comprises two sub-ducts, and
   a run length of each of the two sub-ducts extending to a respective one of the two outlets is the same.

4. The device as recited in claim 3, wherein,
   the sample gas duct further comprises a first sample gas duct section which is defined at the boundary wall, the first sample gas duct section being configured to extend to a central axis arranged between the two axial ends of the gas cell,
   the first sample gas duct section divides into the two sub-ducts at the central axis, and
   the two sub-ducts each extend to the a respective one of the two axial ends.

5. The device as recited in claim 4, wherein,
   the gas cell further comprises a base plate,
   the boundary wall of the gas cell is a base, and
   the sample gas duct is defined at the base and is closed by the base plate.

6. The device as recited in claim 5, wherein,
   the gas cell further comprises axial boundary walls,
   the sample gas duct is further configured to extend until directly before the axial boundary walls, and
   each of the two outlets enter the chamber on an axial central axis of the gas cell.

7. The device as recited in claim 6, further comprising:
   object or field mirrors,
   wherein,
   the two outlets of the sample gas duct are each configured to enter the chamber axially between the object or field mirrors and the axial boundary walls.

8. The device as recited in claim 6, wherein,
   the gas cell further comprises side walls; and
   the heating source is defined by a heating mat arranged in the side walls.

9. The device as recited in claim 8, wherein the heating source is defined by a plurality of electric heating rods arranged in the side walls.

10. The device as recited in claim 9, wherein,
    the side walls comprise vertically extending bores, and
    the plurality of heating rods are arranged in the vertically extending bores.

11. The device as recited in claim 8, further comprising:
    a temperature sensor,
    wherein,
    the gas cell further comprises a lid, and
    the temperature sensor is arranged in at least one of the axial boundary walls, the side walls, the lid, and the base.

12. The device as recited in claim 11, wherein the axial boundary walls, the side walls, the lid, and the base are made of a material comprising a heat conductivity of more than 12 W/mK.

13. The device as recited in claim 1, wherein the sample gas duct is further configured to comprise a meander-shape.

* * * * *